United States Patent [19]

Rentzea et al.

[11] Patent Number: 4,944,789
[45] Date of Patent: Jul. 31, 1990

[54] AZETIDINE DERIVATIVE AND THEIR USE FOR REGULATING PLANT GROWTH

[75] Inventors: Costin Rentzea, Heidelberg; Wilhelm Rademacher; Johann Jung, both of Limburgerhof; Albrecht Harreus, Ludwigshafen, all of Fed. Rep. of Germany

[73] Assignee: BASF Aktiengesellschaft, Ludwigshafen, Fed. Rep. of Germany

[21] Appl. No.: 376,994

[22] Filed: Jul. 7, 1989

[30] Foreign Application Priority Data

Jul. 15, 1988 [DE] Fed. Rep. of Germany ....... 3824052
May 19, 1989 [DE] Fed. Rep. of Germany ....... 3916364

[51] Int. Cl.$^5$ .................. A01N 43/34; C07D 205/04
[52] U.S. Cl. .......................................... 71/88; 548/953
[58] Field of Search ............................ 548/953; 71/88

[56] References Cited

U.S. PATENT DOCUMENTS 3,156,554 11/1964 Tolbert ................................. 71/86

OTHER PUBLICATIONS

Black et al., Chem. Abst. 89-24064n(1978).
Black et al., Chem. Abst. 92-75494X(1980).

*Primary Examiner*—Cecilia Shen
*Attorney, Agent, or Firm*—Oblon, Spivak, McClelland, Maier & Neustadt

[57] ABSTRACT

Azetidine derivatives of the formula I

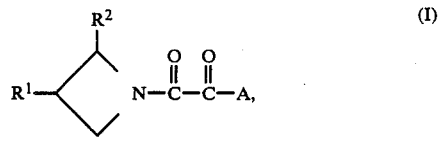

where $R^1$ and $R^2$ are each hydrogen or $C_1$–$C_3$-alkyl, A is —$XR^3$ or —$N(R^5)$—$OR^4$, X is oxygen or sulfur, $R^3$ is $C_1$–$C_{20}$-alkyl, $C_1$–$C_{20}$-haloalkyl, $C_3$–$C_{18}$-alkenyl, $C_3$- or $C_4$-alkynyl, bridged $C_3$–$C_{12}$-cycloalkyl or $C_4$–$C_{12}$-alkylcycloalkyl, the cycloalkyl radicals or alkylcycloalkyl radicals being unsubstituted or substituted by $C_1$–$C_5$-alkyl or cyclohexyl, $R^4$ is $C_1$–$C_{20}$-alkyl, $C_1$–$C_{12}$-haloalkyl, $C_1$–$C_6$-cyanoalkyl, $C_1$–$C_{12}$-alkoxyalkyl, $C_3$–$C_{18}$-alkenyl, $C_3$–$C_{18}$-haloalkenyl, $C_3$- or $C_4$-alkynyl, $C_3$–$C_{12}$-cycloalkyl or $C_4$–$C_{12}$-cycloalkylalkyl, $C_3$–$C_{16}$-alkoxycarbonylalkyl or unsubstituted or substituted $C_7$–$C_{20}$-aralkyl and $R^5$ is hydrogen or $C_1$–$C_3$-alkyl, and agents and methods for regulating plant growth.

5 Claims, No Drawings

AZETIDINE DERIVATIVE AND THEIR USE FOR REGULATING PLANT GROWTH

The present invention relates to novel azetidine derivatives of the general formula I

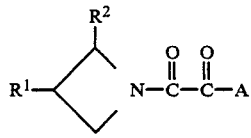

where $R^1$ and $R^2$ are each hydrogen or $C_1$–$C_3$-alkyl, A is —$XR^3$ or —$N(R^5)$—$OR^4$, X is oxygen or sulfur, $R^3$ is $C_1$–$C_{20}$-alkyl, $C_1$–$C_{20}$-haloalkyl, $C_3$–$C_{18}$-alkenyl, $C_3$- or $C_4$-alkynyl, $C_3$–$C_{12}$-cycloalkyl, bridged $C_3$–$C_{12}$-cycloalkyl or $C_4$–$C_{12}$-alkylcycloalkyl, the cycloalkyl radicals or alkylcycloalkyl radicals being unsubstituted or substituted by $C_1$–$C_5$-alkyl or cyclohexyl, $R^4$ is $C_1$–$C_{20}$-alkyl, $C_1$–$C_{12}$-haloalkyl, $C_1$–$C_6$-cyanoalkyl, $C_1$–$C_{12}$-alkoxyalkyl, $C_3$–$C_{18}$-alkenyl, $C_3$–$C_{18}$-haloalkenyl, $C_3$- or $C_4$-alkynyl, $C_3$–$C_{12}$-cycloalkyl or $C_4$–$C_{12}$-cycloalkylalkyl, $C_3$–$C_{16}$-alkoxycarbonylalkyl or unsubstituted or substituted $C_7$–$C_{20}$-aralkyl and $R^5$ is hydrogen or $C_1$–$C_3$-alkyl, and agents which contain these azetidine derivatives as active ingredients, processes for their preparation and methods for regulating plant growth with these compounds.

It is known that certain 2-haloethyltrialkylammonium halides have plant growth-regulating properties (cf. U.S. Pat. No. 3,156,554). For example, (2-chloroethyl)-trimethylammonium chloride can be used for influencing the growth of cereals (cf. J. Biol. Chem. 235 (1960), 475). However, the activity of this substance is unsatisfactory, at least in certain target organisms, in terms of application rate, level of side effects and morphospecific action.

It is an object of the present invention to provide novel compounds which have a high bioregulatory activity, in particular plant growth-regulating activity, and are well tolerated by plants.

We have found that this object is achieved by the azetidine derivatives I defined at the outset and processes for their preparation. We have also found agents which contain these azetidine derivatives as active ingredients and a method for regulating plant growth with these compounds.

Specifically, the radicals $R^1$ to $R^5$ in formula I have the following meanings:

$R^1$ and $R^2$ are identical or different and are each propyl, isopropyl, preferably ethyl, methyl or hydrogen. Compounds in which one or more of the radicals $R^1$ or $R^2$ are hydrogen are preferred.

$R^3$ can be varied widely. $R^3$ is, for example, straight-chain or branched $C_1$–$C_{20}$-alkyl, in particular $C_1$–$C_{16}$-alkyl, such as methyl, ethyl, n-propyl, isopropyl, n-butyl, isobutyl, sec-butyl, pentyl, hexyl, heptyl, octyl, nonyl, decyl, undecyl, tridecyl, tetradecyl, pentadecyl, hexadecyl, heptadecyl, octadecyl or nonadecyl; straight-chain or branched $C_1$–$C_{20}$-haloalkyl, in particular $C_1$–$C_{12}$-haloalkyl having 1 to 3, preferably 1 or 2, halogen atoms, such as iodine or bromine, in particular fluorine or chlorine, for example chlorobutyl, such as 1-chlorobutyl, 2-chlorobutyl, 3-chlorobutyl, 4-chlorobutyl or 2,3-dichlorobutyl, chlorohexyl, such as 3-chlorohexyl or 5-chlorohexyl, fluoropentyl, such as 3-fluoropentyl, fluorohexyl, fluoroheptyl, fluorodecyl or fluorododecyl; $C_3$–$C_{18}$-alkenyl, in particular $C_3$–$C_{16}$-alkenyl having 1 to 3 double bonds in the alkenyl radical, such as allyl, methallyl, pentenyl, hexenyl, heptenyl, octenyl, decenyl, dodecenyl, geranyl, hexadecenyl or octadecenyl; $C_3$- or $C_4$-alkynyl, such as propargyl or 2-butynyl; $C_3$–$C_{12}$-cycloalkyl or $C_4$–$C_{12}$-alkylcycloalkyl, in particular $C_3$–$C_8$-cycloalkyl or $C_4$–$C_{10}$-alkylcycloalkyl, which may be bridged, i.e. may carry one or two methylene or ethylene bridges, the stated cycloalkyl or alkylcycloalkyl radicals being unsubstituted or $C_1$–$C_5$-alkyl-substituted or cyclohexyl-substituted. Examples are cycloalkyl, such as cyclopropyl, cyclopentyl, methylcyclopentyl, cyclohexyl, ethylcyclohexyl, propylcyclohexyl, isopropylcyclohexyl, butylcyclohexyl, isobutylcyclohexyl, sec-butylcyclohexyl and tert-butylcyclohexyl, tert-amylcyclohexyl, cyclohexylcyclohexyl, cycloheptyl, methylcycloheptyl, propylcycloheptyl, cyclooctyl, cyclododecyl and decalyl (decahydronaphthyl); alkylcycloalkyl, in particular cycloalkyl-substituted methyl, such as cyclopropylmethyl, cyclopentylmethyl, cyclohexylmethyl or cyclododecylmethyl; bridged cycloalkyl or alkylcycloalkyl, such as norbornyl, 1,5-dimethylbicyclo[2.3.1]oct-8-yl, tricyclodecyl, norbornylmethyl or adamantyl, and mono- and bicycloterpene radicals, such as o-menthyl, m-menthyl, p-menthyl, bornyl, isobornyl, pinanyl, camphenyl and homocamphenyl.

$R^4$ can likewise be widely varied. $R^4$ is, for example, straight-chain or branched $C_1$–$C_{20}$-alkyl, in particular $C_1$–$C_{16}$-alkyl, such as methyl, ethyl, n-propyl, isopropyl, n-butyl, isobutyl, sec-butyl, pentyl, hexyl, heptyl, octyl, nonyl, decyl, undecyl, dodecyl, tridecyl, tetradecyl, pentadecyl, hexadecyl, heptadecyl, octadecyl or nonadecyl; straight-chain or branched $C_1$–$C_{12}$-haloalkyl having 1 to 3, preferably 1 or 2, halogen atoms, such as iodine or bromine, in particular fluorine or chlorine, for example chlorobutyl, such as 1-chlorobutyl, 2-chlorobutyl, 3-chlorobutyl, 4-chlorobutyl or 2,3-dichlorobutyl, chlorohexyl, such as 3-chlorohexyl or 5-chlorohexyl, fluoropentyl, such as 3-fluoropentyl, or fluorohexyl, fluoroheptyl, fluorodecyl or fluorododecyl; $C_1$–$C_6$-cyanoalkyl, in particular $C_1$–$C_4$-cyanoalkyl having one cyano group, e.g. cyanomethyl, cyanoethyl or cyanopropyl;

$C_1$–$C_{12}$-alkoxyalkyl, in particular alkoxy-substituted $C_1$–$C_8$-alkyl, particularly suitable alkoxy radicals being $C_1$–$C_4$-alkoxy, such as methoxy, ethoxy, propoxy, isopropoxy, butoxy, isobutoxy, sec-butoxy or tert-butoxy; $C_3$–$C_{18}$-alkenyl, in particular $C_3$–$C_{16}$-alkenyl having 1 to 3 double bonds in the alkenyl radical, such as allyl, methallyl, pentenyl, hexenyl, heptenyl, octenyl, decenyl, dodecenyl, geranyl, hexadecenyl or octadecenyl;

$C_3$–$C_{18}$-haloalkenyl, in particular $C_3$–$C_{12}$-haloalkenyl having 1 to 3 double bonds in the alkenyl moiety and one or more, in particular 1 to 3, halogen substituents, such as iodine or bromine, in particular fluorine or chlorine. Examples are trifluoromethyl, trichloromethyl, tribromomethyl, difluorochloromethyl, difluoromethyl, pentafluoroethyl, pentachloroethyl, 1,1,2,2-tetrafluoroethyl, 1,2,2-trifluoro-1,2-dichloroethyl or 1-trifluoromethyl-2,2,2-trifluoroethyl;

$C_3$- or $C_4$-alkynyl, such as propargyl or 2-butynyl;

$C_3$–$C_{12}$-cycloalkyl or $C_4$–$C_{12}$-cycloalkylalkyl, in particular $C_3$–$C_8$-cycloalkyl or $C_4$–$C_{10}$-cycloalkylalkyl, where the stated cycloalkyl or cycloalkylalkyl radicals may be $C_1$–$C_5$-alkyl-substituted or cyclohexyl-substituted. The following radicals are examples: cycloalkyl, such as cyclopropyl, cyclopentyl, methylcyclopentyl, cyclohexyl, ethylcyclohexyl, propylcyclohexyl, isopropylcyclohexyl, butylcyclohexyl, isobutylcyclohexyl, sec-butylcyclohexyl and tert-butylcyclohexyl, tert-amylcyclohexyl, cyclohexylcyclohexyl, cycloheptyl, methylcycloheptyl, propylcycloheptyl, cyclooctyl, cyclododecyl and di-, tri- and tetramethylcyclohexyl; cycloalkylalkyl, in particular cycloalkyl-substituted methyl, such as cyclopropylmethyl, cyclopentylmethyl, cyclohexylmethyl, cycloheptylmethyl, cyclododecylmethyl, cyclohexylethyl and cyclohexylpropyl; $C_3$-$C_{16}$-alkoxycarbonylalkyl, e.g. $C_1$-$C_4$-alkoxycarbonyl-$C_1$-$C_4$-alkyl, $C_1$-$C_4$-alkyl in the alkoxy or alkyl moiety being methyl, ethyl, propyl, isopropyl, butyl or isobutyl; or $C_7$-$C_{20}$-aralkyl, in particular $C_7$-$C_{12}$-phenylalkyl, such as benzyl, 2-phenylethyl, 3-phenylpropyl or 2-phenylpropyl, the aromatic radicals being unsubstitued or substituted by one or more, in particular 1 to 3, substituents, such as halogen, in particular fluorine, chlorine or bromine, nitro, haloalkyl, e.g. fluoro- or chloro-$C_1$-$C_4$-alkyl, such as trifluoromethyl, $C_1$-$C_4$-alkyl or -alkoxy, such as methyl, ethyl, propyl, isopropyl, n-butyl, isobutyl, sec-butyl or tert-butyl or the corresponding alkoxy radicals.

Examples are 4-fluorobenzyl, 4-chlorobenzyl, 4-bromobenzyl, 2,4-dichlorobenzyl, 2-methylbenzyl, 3-methylbenzyl, 4-methylbenzyl, 3-methoxybenzyl, 4-methoxybenzyl, 4-nitrobenzyl, 3-trifluoromethylbenzyl, 4-trifluoromethylbenzyl, 4-tert-butylbenzyl and 2,4,6-trimethylbenzyl.

Where A is $XR^3$, the novel compounds can be prepared by reacting (a) an azetidine of the formula II

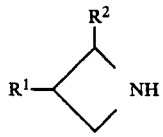 (II)

with an oxalic ester chloride of the formula III

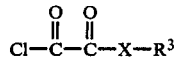 (III)

where $R^1$, $R^2$, X and $R^3$ have the abovementioned meanings, or (b) an oxalamide chloride of the formula IV

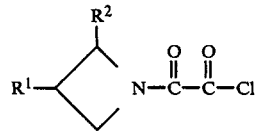 (IV)

with an alcohol or thiol of the formula V

 (V)

where $R^1$, $R^2$, X and $R^3$ have the abovementioned meanings, in the presence or absence of a solvent or diluent and/or of an inorganic or organic base and/or of a reaction accelerator.

Where A is $NR^5$—$OR^4$, the novel compounds can be prepared by reacting (a) an oxalamide chloride of the formula IV

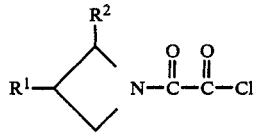 (IV)

with a hydroxylamine derivative of the formula VI

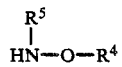 (VI)

where $R^1$, $R^2$, $R^4$ and $R^5$ have the abovementioned meanings, or (b) an oxalamide ester of the formula VII

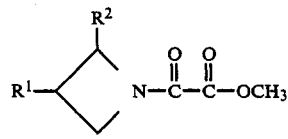 (VII)

with a hydroxylamine derivative of the formula VI

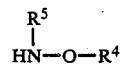 (VI)

where $R^1$, $R^2$, $R^4$ and $R^5$ have the abovementioned meanings, in the presence or absence of a solvent or diluent and/or of an inorganic or organic base and/or of a reaction accelerator.

For both process variants (a) and (b), where A is $XR^3$ or $NR^5$—$OR^4$, suitable solvents or diluents are, for example, halohydrocarbons, in particular chlorohydrocarbons, e.g. tetrachloroethylene, 1,1,2,2- or 2,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o-, p- or m-dichlorobenzene, o-, m- or p-chlorotoluene or 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole or $\beta,\beta,\beta'$-dichlorodiethyl ether; nitrohydrocarbons, such as nitromethane, nitroethane, nitrobenzene, o-, m- or p-chloronitrobenzene or o-nitrotoluene; nitriles, such as acetonitrile, butyronitrile, isobutyronitrile, benzonitrile or m-chlorobenzonitrile; aliphatic or cycloaliphatic hydrocarbons, e.g. heptane, pinane, nonane, o-, m- or p-cumene, gasoline fractions boiling within a range of 70° to 190° C., cyclohexane, methylcyclohexane, decalin, petroleum ether, hexane, naphtha, 2,2,4-trimethylpentane, 2,2,3-trimethylpentane, 2,3,3-trimethylpentane or octane; esters, e.g. ethyl acetate, ethylacetoacetate or isobutyl acetate; amides, e.g. formamide, methylformamide or dimethylformamide; ketones, e.g. acetone or methyl ethyl ketone, and, if required, also water and mixtures of these. The compounds of the formulae III to V or IV, VI and VII can also be used in excess as solvents. Advantageously, the solvent is used in an amount of from 100 to 2,000, preferably from 200 to 700, % by weight, based on starting material II where A is $XR^3$ or based on starting material IV or VII where A is $NR^5$—$OR^4$.

All conventional acid acceptors can be used as inorganic or organic bases for the reaction to give compounds of the formula I. These preferably include tertiary amines, alkaline earth metal compounds, ammonium compounds and alkali metal compounds as well as mixtures of these.

Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec-butylamine, tri-tert-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylmorpholine, N-ethylmorpholine, N-methylhexamethyleneimine, N-ethylhexamethyleneimine, pyridine, quinoline, alpha-picoline, beta-picoline, gamma-picoline, isoquinoline, pyrimidine, acridine, N,N,N',N'-tetramethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

The acid acceptor is advantageously used in stoichiometric amounts or in an amount which is not more than 20 mol %, based on the starting material III where A is $XR^3$ or based on the starting material IV where A is $NR^5$—$OR^4$, greater than or less than the stoichiometric amount.

Preferred reaction accelerators are metal halides, in particular alkali metal halides, such as sodium iodide or potassium iodide.

The Examples which follow illustrate the preparation of the novel active ingredients:

EXAMPLE 1.1

Azetidinoxamide Butyl Ester 15.5 g (0.15 mole) of triethylamine, 8.6 g (0.15 mole) of azetidine and 24.7 g (0.15 mole) of butoxyoxalyl chloride are added in succession to 200 ml of methylene chloride at from 10° to 20° C. The mixture is stirred for 10 hours at 25° C., after which it is washed twice with water, dried over $Na_2SO_4$ and then subjected to fractional distillation. 18.8 g (67.7% of theory) of butyl azetidinoxamate are obtained as a colorless liquid of boiling point 122°–123° C./0.45 mbar and $n_D^{21}$ 1.4702.

The compounds of the formula I which are listed below can be obtained by choosing the relevant starting materials and appropriately adapting the process conditions:

TABLE 1

Compounds of the general formula I where A = $XR^3$ (I)

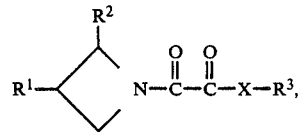

| No. | $R^1$ | $R^2$ | X | $R^3$ | Refractive index, mp (°C.) or bp. (°C./mbar) |
|---|---|---|---|---|---|
| 1.1 | H | H | O | —$C_4H_9$ | 122–123/0.45 |
| 1.2 | H | H | O | —$CH_3$ | 96–98/0.4 |
| 1.3 | H | H | S | —$C_2H_5$ | $n_D^{22}$ 1.5340 |
| 1.4 | H | H | O | —$C_2H_5$ | 98–101/0.1 |
| 1.5 | $CH_3$ | H | O | —$C_2H_5$ | 129–131/0.3 |
| 1.6 | $C_2H_5$ | H | O | —$C_2H_5$ | 136–140/0.2 |
| 1.7 | H | H | O | —$CH_2$—$CH_2$—Cl | $n_D^{23}$ 1.4999 |
| 1.8 | H | H | O | -n-$C_3H_7$ | 106–110/0.12 |
| 1.9 | H | $CH_3$ | O | -n-$C_3H_7$ | 128–131/0.3 |
| 1.10 | H | H | S | -n-$C_3H_7$ | $n_D^{22}$ 1.5266 |
| 1.11 | H | H | O | —$CH_2$—CH=$CH_2$ | 106–110/0.3 |
| 1.12 | H | H | S | —$CH_2$—CH=$CH_2$ | 116–118/0.15 |
| 1.13 | H | H | O | | mp. 67–69 |
| 1.14 | H | H | S | -n-$C_4H_9$ | $n_D^{22}$ 1.5200 |
| 1.15 | $CH_3$ | H | O | -n-$C_4H_9$ | 129–132/0.2 |
| 1.16 | H | H | O | -i-$C_4H_9$ | 106–110/0.1 |
| 1.17 | H | H | O | sec.-$C_4H_9$ | 112–115/0.15 |
| 1.18 | H | H | O | tert.-$C_4H_9$ | 98–105/0.1 |
| 1.19 | H | H | O | —$CH_2$—C($CH_3$)=$CH_2$— | 111–114/0.3 |
| 1.20 | H | H | O | —$CH_2$—CH=CH—$CH_3$(trans) | 123–124/0.3 |
| 1.21 | H | H | O | n-$C_5H_{11}$ | 117–119/0.2 |
| 1.22 | H | H | O | —$CH_2$—$CH_2$—CH($CH_3$)$_2$ | 125–130/0.3 |
| 1.23 | H | H | O | —cyclopentyl | 112–117/0.2 |
| 1.24 | H | H | O | —$CH_2$—CH=C($CH_3$)$_2$ | 127–130/0.3 |
| 1.25 | H | H | O | —$CH_2$—CH=CH—$CH_2$—$CH_3$(trans) | 122–128/0.15 |
| 1.26 | H | H | O | n-$C_6H_{13}$ | 120–122/0.1 |
| 1.27 | H | H | O | -cyclopentylmethyl | 129–132/0.2 |
| 1.28 | H | H | O | -cyclohexyl | 125–128/0.15 |

TABLE 1-continued

Compounds of the general formula I where A = XR³

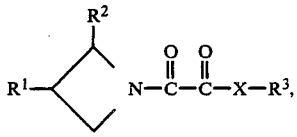

| No. | R¹ | R² | X | R³ | Refractive index, mp (°C.) or bp. (°C./mbar) |
|---|---|---|---|---|---|
| 1.29 | H | H | O | —C₆H₁₃ | 132–135/0.15 |
| 1.30 | H | H | O | —(CH₂)₆—Cl | 127–129/0.2 |
| 1.31 | H | H | O | -cyclohexylmethyl | 138–139/0.15 |
| 1.32 | H | H | O | cycloheptyl | 132–135/0.1 |
| 1.34 | H | H | O | n-C₈H₁₇ | $n_D^{22}$ 1.4682 |
| 1.35 | H | H | O | —CH₂—CH(C₂H₅)—(CH₂)₃—CH₃ | 152–157/0.25 |
| 1.36 | H | H | O | -geranyl | oil |
| 1.37 | H | H | O | -cyclohexylethyl | 144–147/0.2 |
| 1.38 | H | H | O | -menthyl | 131–135/0.1 |
| 1.39 | H | H | O | -norbornyl | 128–129/0.1 |
| 1.40 | H | H | O | -pinanyl | 131–135/0.3 |
| 1.41 | H | H | O | -4-tert.-butylcyclohexyl | 149–152/0.3 |
| 1.42 | H | H | O | n-C₉—H₁₉ | $n_D^{28}$ 1.4686 |
| 1.43 | H | H | O | n-C₁₀H₂₁ | mp. 36–38 |
| 1.44 | H | H | O | -9-decen-1-yl | mp. 30–32 |
| 1.45 | H | H | O | n-C₁₂H₂₅ | mp. 47–48 |
| 1.46 | H | H | O | n-C₁₄H₂₉ | mp. 55–56 |
| 1.47 | H | H | O | n-C₁₆H₃₃ | mp. 61–62 |

EXAMPLE 2.1

O-(2-Methyl-2-propen-1-yl)-azetidinoxamide-hydroxamic acid

At 25° C., 14.3 g (0.1 mol) of azetidineoxamide methyl ester, followed by 18.5 g (0.15 mol) of O-(2-methyl-2-propen-1-yl)-hydroxylamine hydrochloride and then by 15 g (0.15 mol) of triethylamine were added to 100 ml of methanol. The mixture was stirred for 10 hours at 25° C. and for a further 10 hours at 70° C., and then concentrated. 200 ml of methanol was added to the residue, and the whole was washed three times with water, dried over Na₂SO₄ and concentrated under reduced pressure. 20 ml of ether was added to the residue, and the crystals were suction filtered and dried. There was obtained 12.4 g (62.6% of theory) of O-(2-methyl-2-propen-1-yl)-azetinedioxamide-hydroxamic acid as white crystals of melting point 92°–94° C.

By appropriate selection of the starting materials and adapting the process conditions accordingly, the compounds of the formula I listed below may be obtained:

TABLE 2

Compounds of the general formula I where A = —N(R⁵)—OR⁴

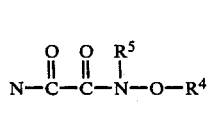

| Example No. | R¹ | R² | R⁵ | R⁴ | mp (°C.) or bp. (°C./mbar) |
|---|---|---|---|---|---|
| 2.2 | H | H | H | H | 149–151 |
| 2.3 | H | CH₃ | H | H | 91–92 |
| 2.4 | H | H | H | CH₃ | 103–105 |
| 2.5 | H | H | H | C₂H₅ | 73–77 |
| 2.6 | H | H | H | C₃H₇-n | 66–67 |
| 2.7 | H | CH₃ | H | C₃H₇-n | 137–140/0.3 |
| 2.8 | CH₃ | CH₃ | H | C₃H₇-n | 141–145/0.2 |
| 2.9 | H | H | CH₃ | CH₃ | 97–100 |
| 2.10 | H | H | H | CH₂—CH=CH₂ | 114–117 |
| 2.11 | H | H | H | CH₂—CH=CH—CH₃ | 138–140 |
| 2.12 | H | H | H | CH₂—CH=CH—Cl | 145–148 |

TABLE 2-continued

Compounds of the general formula I where A = —N(R⁵)—OR⁴

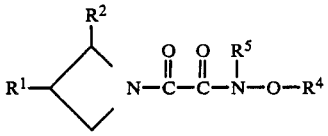

| Example No. | R¹ | R² | R⁵ | R⁴ | mp (°C.) or bp. (°C./mbar) |
|---|---|---|---|---|---|
| 2.13 | H | H | H | CH₂—C(Cl)=CH₂ | 93–96 |
| 2.14 | H | H | H | CH₂—C≡CH | 120–123 |
| 2.15 | H | H | H | C₄H₉-n | 62–64 |
| 2.16 | H | CH₃ | H | C₄H₉-n | 142–153/0.2 |
| 2.17 | H | H | H | C₅H₁₁-n | 80–83 |
| 2.18 | H | H | H | C₆H₁₃-n | 89–92 |
| 2.19 | H | H | H | (CH₂)₃—Cl | 59–62 |
| 2.20 | H | H | H | (CH₂)₄—Cl | 75–78 |
| 2.21 | H | H | H | CH₂—C₆H₁₁ | 135–137 |
| 2.22 | H | H | H | CH₂—C₆H₅ | 160–163 |
| 2.23 | H | H | H | 2-Cl—C₆H₄—CH₂ | resin |
| 2.24 | H | H | H | 4-Cl—C₆H₄—CH₂ | 179–182 |

The compounds of the formula I may exercise a variety of influences on practically all plant development stages and are therefore used as growth regulators. The diversity of action of growth regulators depends especially on (a) the type and variety of plant;
(b) the time applied, with reference to the development stage of the plants and the time of the year;
(c) the place and method of application (seed treatment, soil treatment, or application to foliage);
(d) climatic factors, e.g., average temperature, amount of precipitate, sunshine and duration;
(e) soil conditions (including fertilization);
(f) the formulation of the active ingredient; and
(g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With bioregulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with growth-regulating agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The novel agents may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients to be used in accordance with the invention may be applied not only to the seed (as a disinfectant), but also to the soil, i.e., via the roots, and to the foliage.

As a result of the good crop plant tolerance, the application rate may vary considerably. When seed is treated, active ingredient amounts of from 0.001 to 50, and preferably from 0.01 to 10, g per kg of seed are generally needed. When the soil or foliage is treated, rates of from 0.01 to 10, and preferably from 0.05 to 3, kg per hectare are generally considered to be sufficient.

The agents according to the invention may be used in the form of conventional formulations such as solutions, emulsions, suspensions, dusts, powders, pastes and granules. The form of application depends entirely on the purpose for which the agents are being used, but it should at all events ensure a fine and uniform distribution of the active ingredient. The formulations are prepared in known manner, e.g., by extending the active ingredient with solvents and/or carriers, with or without the use of emulsifiers and dispersants; where water is used as diluent, other organic solvents may be used as auxiliary solvents. The most suitable auxiliaries for such purposes are solvents such as aromatics (e.g., xylene, benzene), chlorinated aromatics (e.g., chlorobenzenes), paraffins (e.g., oil fractions), alcohols (e.g., methanol, butanol), amines (e.g., ethanolamine), N,N-dimethylformamide and water; solid carriers such as natural rock flours (e.g., kaolins, diatomaceous earths, talc and chalk) and synthetic rock flours (e.g., highly disperse silicic acid, silicates); emulsifiers and other surfactants, such as non-ionic and anionic emulsifiers (e.g., polyoxyethylene fatty alcohol ethers, alkyl sulfonates) and dispersants such as lignin, sulfite waste liquors and methyl cellulose. It is preferred to use the compounds according to the invention in aqueous solution, with or without the addition of water-miscible organic solvents such as methanol or other lower alcohols, acetone, N,N-dimethylformamide and N-methylpyrrolidone. The formulations generally contain from 0.1 to 95, and preferably from 0.5 to 90, wt % of active ingredient.

The formulations, and ready-to-use application forms prepared therefrom, such as solutions, emulsions, suspensions, powders, dusts, pastes and granules, are applied in known manner, for instance preemergence, post-emergence or as seed dressings.

Examples of formulations are given below:

I. 20 parts by weight of the compound of Example 1.1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of the compound of Example 1.13 is intimately mixed with 97 parts by weight of particulate kaolin. A dust is obtained containing 3% by weight of the active ingredient.

III. 30 parts by weight of the compound of Example 1.1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 20 parts of the compound of Example 8.2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 90 parts by weight of the compound of Example 2.1 is mixed with 10 parts by weight of N-methyl-alpha-pyrrolidone. A mixture is obtained which is suitable for application in the form of very fine drops.

VI. 20 parts by weight of the compound of Example 4.4 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

VII. 20 parts by weight of the compound of Example 1.25 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

VIII. 20 parts by weight of the compound of Example 5.2 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

In these application forms, the agents according to the invention may be accompanied by other active ingredients, e.g., herbicides, insecticides, or be mixed and applied with fertilizers. When the agents according to the invention are mixed with other growth regulators, synergistic effects occur, i.e., the action of the combination is greater than the added effects of the individual components.

USE EXAMPLES

To determine the growth-regulating properties of the candidate compounds, a culture medium was supplied with sufficient nutrients, and test plants were grown therein in plastic pots approx. 12.5 cm in diameter and having a volume of about 500 ml.

In the postemergence treatment, the candidate compounds were applied to the plants as aqueous formulations. The growth-regulating action observed was confirmed at the end of the experiment by measuring the growth height. The figures obtained were compared with those for untreated plants.

2-Chloroethyltrimethylammonium chloride (CCC)

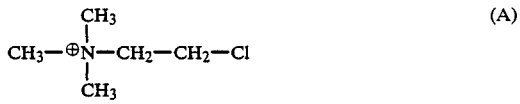
(A)

was used as comparative compound.

Not only was growth height reduced—the leaves also took on a more intense color. The increased chlorophyll content is indicative of a higher rate of photosynthesis, making for bigger yields.

The results are given in the following tables:

TABLE 3

Spring wheat, "Kolibri" variety; postemergence treatment

| No. of chem. example | Active ingr. conc. per vessel [mg] | Relative growth height |
|---|---|---|
| untreated | — | 100 |
| "A" | 0.38 | 95.2 |
|  | 1.5 | 90.3 |
| 1.1 | 0.38 | 91.9 |
|  | 1.5 | 72.5 |
| 1.2 | 0.38 | 77.2 |
|  | 1.5 | 49.6 |
| 1.3 | 0.38 | 78.7 |
|  | 1.5 | 53.9 |
| 1.7 | 0.38 | 84.1 |
|  | 1.5 | 60.8 |
| 1.8 | 0.38 | 90.6 |
|  | 1.5 | 79.0 |
| 1.10 | 0.38 | 78.7 |
|  | 1.5 | 52.5 |
| 1.11 | 0.38 | 82.9 |
|  | 1.5 | 64.7 |
| 1.12 | 0.38 | 75.8 |
|  | 1.5 | 49.6 |
| 1.13 | 0.38 | 84.1 |
|  | 1.5 | 63.4 |
| 1.14 | 0.38 | 75.8 |
|  | 1.5 | 43.7 |
| 1.16 | 0.38 | 90.6 |
|  | 1.5 | 80.3 |
| 1.19 | 0.38 | 85.4 |
|  | 1.5 | 68.6 |
| 1.20 | 0.38 | 85.4 |
|  | 1.5 | 64.7 |
| 1.21 | 0.38 | 89.3 |
|  | 1.5 | 66.0 |
| 1.24 | 0.38 | 88.0 |
|  | 1.5 | 64.7 |
| 1.26 | 0.38 | 84.1 |
|  | 1.5 | 63.4 |
| 1.27 | 0.38 | 83.9 |
|  | 1.5 | 72.6 |
| 1.34 | 0.38 | 82.3 |
|  | 1.5 | 66.1 |
| 1.36 | 0.38 | 88.0 |
|  | 1.5 | 69.9 |
| 1.42 | 0.38 | 79.0 |
|  | 1.5 | 64.5 |
| 1.43 | 0.38 | 82.3 |
|  | 1.5 | 69.4 |
| 1.45 | 0.38 | 85.5 |
|  | 1.5 | 75.8 |
| 1.46 | 0.38 | 93.6 |
|  | 1.5 | 88.7 |

TABLE 4

Spring barley, "Aramir" variety; postemergence treatment

| No. of chem. example | Active ingr. conc. per vessel [mg] | Relative growth height |
|---|---|---|
| untreated | — | 100 |
| "A" | 0.38 | 94.5 |
|  | 1.5 | 94.5 |
| 1.1 | 0.38 | 89.0 |
|  | 1.5 | 60.6 |
| 1.2 | 0.38 | 87.6 |
|  | 1.5 | 65.0 |
| 1.3 | 0.38 | 87.6 |
|  | 1.5 | 66.4 |
| 1.7 | 0.38 | 87.8 |
|  | 1.5 | 56.9 |
| 1.8 | 0.38 | 89.0 |
|  | 1.5 | 64.3 |
| 1.10 | 0.38 | 90.5 |
|  | 1.5 | 67.9 |
| 1.11 | 0.38 | 80.4 |
|  | 1.5 | 54.4 |
| 1.12 | 0.38 | 87.6 |
|  | 1.5 | 60.8 |
| 1.13 | 0.38 | 85.3 |
|  | 1.5 | 59.4 |
| 1.14 | 0.38 | 84.8 |
|  | 1.5 | 53.7 |
| 1.16 | 0.38 | 90.3 |
|  | 1.5 | 59.4 |
| 1.19 | 0.38 | 87.8 |
|  | 1.5 | 51.9 |
| 1.20 | 0.38 | 86.6 |
|  | 1.5 | 51.9 |
| 1.21 | 0.38 | 84.1 |
|  | 1.5 | 49.5 |
| 1.24 | 0.38 | 85.3 |
|  | 1.5 | 59.4 |
| 1.26 | 0.38 | 85.3 |
|  | 1.5 | 53.2 |
| 1.27 | 0.38 | 85.0 |
|  | 1.5 | 50.4 |
| 1.34 | 0.38 | 85.0 |
|  | 1.5 | 50.4 |
| 1.36 | 0.38 | 87.8 |
|  | 1.5 | 58.1 |
| 1.42 | 0.38 | 80.3 |
|  | 1.5 | 53.5 |
| 1.43 | 0.38 | 81.9 |
|  | 1.5 | 53.5 |
| 1.45 | 0.38 | 80.3 |
|  | 1.5 | 59.8 |
| 1.46 | 0.38 | 86.6 |
|  | 1.5 | 69.3 |

TABLE 5

Spring wheat, "Kolibri" variety; postemergence treatment

| No. of chem. example | Active ingr. conc. per vessel [mg] | Relative growth height |
|---|---|---|
| untreated | — | 100 |
| "A" | 1.5 | 90.3 |
|  | 6 | 87.1 |
| 1.4 | 1.5 | 66.5 |
|  | 6 | 48.7 |

TABLE 6

Spring barley, "Aramir" variety; postemergence treatment

| No. of chem. example | Active ingr. conc. per vessel [mg] | Relative growth height |
|---|---|---|
| untreated | — | 100 |
| "A" | 1.5 | 94.5 |
|  | 6 | 91.3 |
| 1.4 | 1.5 | 75.1 |
|  | 6 | 40.2 |

TABLE 7

Rice, "Bahia" variety; postemergence treatment

| No. of chem. example | Active ingr. conc. per vessel [mg] | Relative growth height |
|---|---|---|
| untreated | — | 100 |
| "A" | 1.5 | 98.6 |
|  | 3 | 98.6 |
| 1.1 | 1.5 | 73.2 |
|  | 3 | 70.4 |
| 1.7 | 1.5 | 73.2 |
|  | 3 | 67.6 |
| 1.8 | 1.5 | 76.1 |
|  | 3 | 73.2 |
| 1.11 | 1.5 | 70.4 |
|  | 3 | 64.8 |
| 1.13 | 1.5 | 67.6 |
|  | 3 | 64.8 |
| 1.16 | 1.5 | 76.1 |
|  | 3 | 70.4 |
| 1.19 | 1.5 | 70.4 |
|  | 3 | 67.6 |
| 1.20 | 1.5 | 71.8 |
|  | 3 | 66.2 |
| 1.21 | 1.5 | 71.8 |
|  | 3 | 67.6 |
| 1.24 | 1.5 | 73.2 |
|  | 3 | 69.0 |
| 1.26 | 1.5 | 70.4 |
|  | 3 | 63.4 |
| 1.27 | 1.5 | 71.8 |
|  | 3 | 67.6 |
| 1.36 | 1.5 | 71.8 |
|  | 3 | 67.6 |

TABLE 8

Rice, "Bahia" variety; postemergence treatment

| No. of chem. example | Active ingr. conc. per vessel [mg] | Relative growth height |
|---|---|---|
| untreated | — | 100 |
| "A" | 1.5 | 99.8 |
|  | 6 | 97.1 |
| 1.2 | 1.5 | 80.1 |
|  | 6 | 53.8 |
| 1.3 | 1.5 | 81.4 |
|  | 6 | 52.5 |
| 1.10 | 1.5 | 88.0 |
|  | 6 | 52.5 |
| 1.12 | 1.5 | 85.3 |
|  | 6 | 53.8 |
| 1.14 | 1.5 | 88.0 |
|  | 6 | 55.1 |

TABLE 9

Sunflowers, "Sorex" variety; postemergence treatment

| No. of chem. example | Active ingr. conc. per vessel [mg] | Relative growth height |
|---|---|---|
| untreated | — | 100 |
| "A" | 6 | 85.6 |
| 1.4 | 6 | 58.2 |
| 1.7 | 6 | 47.6 |
| 1.19 | 6 | 50.7 |
| 1.24 | 6 | 50.7 |

TABLE 10

Spring rape, "Petranova" variety; postemergence treatment

| No. of chem. example | Active ingr. conc. per vessel [mg] | Relative growth height |
|---|---|---|
| untreated | — | 100 |
| "A" | 1.5 | 94.1 |
|  | 6 | 94.1 |
| 1.2 | 1.5 | 68.6 |
|  | 6 | 68.6 |
| 1.3 | 1.5 | 70.6 |
|  | 6 | 70.6 |

TABLE 10-continued
Spring rape, "Petranova" variety; postemergence treatment

| No. of chem. example | Active ingr. conc. per vessel [mg] | Relative growth height |
|---|---|---|
| 1.10 | 1.5 | 70.6 |
|  | 6 | 70.6 |
| 1.12 | 1.5 | 70.6 |
|  | 6 | 66.7 |
| 1.14 | 1.5 | 70.6 |
|  | 6 | 70.6 |

TABLE 11
Cotton, "Delta Pine" variety; postemergence treatment

| No. of chem. example | Active ingr. conc. per vessel [mg] | Relative growth height |
|---|---|---|
| untreated | — | 100 |
| "A" | 0.5 | 80.1 |
| 1.1 | 0.5 | 71.0 |
| 1.8 | 0.5 | 74.4 |
| 1.11 | 0.5 | 69.8 |
| 1.13 | 0.5 | 64.1 |
| 1.16 | 0.5 | 73.3 |
| 1.19 | 0.5 | 68.7 |
| 1.20 | 0.5 | 75.5 |
| 1.21 | 0.5 | 68.7 |
| 1.24 | 0.5 | 72.1 |
| 1.26 | 0.5 | 74.4 |
| 1.27 | 0.5 | 73.3 |
| 1.36 | 0.5 | 73.3 |

TABLE 12
Indian corn, "Dea" variety; postemergence treatment

| No. of chem. example | Active ingr. conc. per vessel [mg] | Relative growth height |
|---|---|---|
| untreated | — | 100 |
| "A" | 1.5 | 101.1 |
|  | 6 | 101.1 |
| 1.2 | 1.5 | 64.9 |
|  | 6 | 63.4 |
| 1.3 | 1.5 | 69.4 |
|  | 6 | 63.4 |
| 1.4 | 1.5 | 66.4 |
|  | 6 | 63.4 |
| 1.10 | 1.5 | 72.5 |
|  | 6 | 69.4 |
| 1.12 | 1.5 | 66.4 |
|  | 6 | 63.4 |
| 1.14 | 1.5 | 60.4 |
|  | 6 | 60.4 |

TABLE 13
Spring wheat, "Ralle" variety
Postemergence treatment

| No. of chem. example | Active ingr. conc. per vessel [mg] | Relative growth height |
|---|---|---|
| untreated | — | 100 |
| "A" | 6 | 80.6 |
| 2.1 | 6 | 68.8 |

TABLE 14
Spring barley, "Aramir" variety
Postemergence treatment

| No. of chem. example | Active ingr. conc. per vessel [mg] | Relative growth height |
|---|---|---|
| untreated | — | 100 |
| "A" | 1.5 | 93.2 |
|  | 6 | 87.7 |
| 2.1 | 1.5 | 63.0 |
|  | 6 | 49.3 |

TABLE 15
Sunflowers, "Spanners Allzweck" variety
Postemergence treatment

| No. of chem. example | Active ingr. conc. per vessel [mg] | Relative growth height |
|---|---|---|
| untreated | — | 100 |
| "A" | 6 | 82.2 |
| 2.2 | 6 | 72.0 |
| 2.4 | 6 | 73.2 |
| 2.5 | 6 | 73.2 |
| 2.10 | 6 | 76.2 |

TABLE 16
Rice, "Bahia" variety
Postemergence treatment

| No. of chem. example | Active ingr. conc. per vessel [mg] | Relative growth height |
|---|---|---|
| untreated | — | 100 |
| "A" | 1.5 | 99.7 |
|  | 6 | 94.1 |
| 2.1 | 1.5 | 91.4 |
|  | 6 | 63.7 |

TABLE 17
Indian corn, "Inrakorn" variety
Postemergence treatment

| No. of chem. example | Active ingr. conc. per vessel [mg] | Relative growth height |
|---|---|---|
| untreated | — | 100 |
| "A" | 3 | 93.1 |
|  | 6 | 93.1 |
| 2.1 | 3 | 66.8 |
|  | 6 | 62.7 |

We claim:

1. Azetidine compound of the formula I

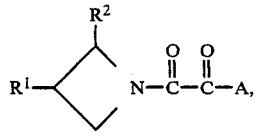

(I)

where $R^1$ and $R^2$ are each hydrogen or $C_1$–$C_3$-alkyl, A is —$XR^3$ or —$N(R^5)$—$OR^4$, X is oxygen or sulfur, $R^3$ is $C_1$–$C_{20}$-alkyl, $C_1$–$C_{20}$-haloalkyl, $C_3$–$C_{18}$-alkenyl, $C_3$- or $C_4$-alkynyl, bridged $C_3$–$C_{12}$-cycloalkyl or $C_4$–$C_{12}$-alkylcycloalkyl, the cycloalkyl radicals or alkylcycloalkyl radicals being unsubstituted or substituted by $C_1$–$C_5$-alkyl or cyclohexyl, $R^4$ is $C_1$–$C_{20}$-alkyl, $C_1$–$C_{12}$-haloalkyl, $C_1$–$C_6$-cyanoalkyl, $C_1$–$C_{12}$-alkoxyalkyl, $C_3$–$C_{18}$-alkenyl, $C_3$–$C_{18}$haloalkenyl, $C_3$- or $C_4$-alkynyl, $C_3$–$C_{12}$-cycloalkyl or $C_4$–$C_{12}$-cycloalkylalkyl, $C_3$–$C_{1-6}$alkoxycarbonylalkyl or $C_7$–$C_{20}$-aralkyl being unsubstituted or substituted on the aromatic group by halogen, nitro, halo-$C_1$–$C_4$-alkyl, $C_1$–$C_4$-alkyl or $C_1$–$C_4$-alkoxy, and $R^5$ is hydrogen or $C_1$–$C_3$-alkyl.

2. An agent for regulating plant growth, containing an effective amount of an azetidine compound of the formula I as set forth in claim 1 and conventional inert additives.

3. An agent for regulating plant growth, containing from 0.1 to 95 wt % of an azetidine compound of the formula I as set forth in claim 1 and conventional inert additives.

4. A process for regulating plant growth, wherein the soil, the plants or the seed are treated with an azetidine compound of the formula I as set forth in claim 1.

5. A process for regulating plant growth, wherein an effective amount of at least one azetidine compound of the formula I as set forth in claim 1 is allowed to act on plants or their habitat.

* * * * *